(12) United States Patent
Gallacher et al.

(10) Patent No.: US 11,419,498 B2
(45) Date of Patent: Aug. 23, 2022

(54) METHODS AND APPARATUS FOR USING BRAIN IMAGING TO PREDICT PERFORMANCE

(71) Applicant: Voxel AI, Inc., Toronto (CA)

(72) Inventors: Benjamin J. A. Gallacher, Toronto (CA); Douglas J. Cook, Toronto (CA); Chris I. Murray, Toronto (CA); Andrew N. Ross, Toronto (CA)

(73) Assignee: Voxel AI, Inc., Toronto (CA)

( * ) Notice: Subject to any disclaimer, the term of this patent is extended or adjusted under 35 U.S.C. 154(b) by 226 days.

(21) Appl. No.: 16/756,286

(22) PCT Filed: Oct. 16, 2018

(86) PCT No.: PCT/IB2018/001307
§ 371 (c)(1),
(2) Date: Apr. 15, 2020

(87) PCT Pub. No.: WO2019/077410
PCT Pub. Date: Apr. 25, 2019

(65) Prior Publication Data
US 2020/0297210 A1    Sep. 24, 2020

Related U.S. Application Data

(60) Provisional application No. 62/573,027, filed on Oct. 16, 2017.

(51) Int. Cl.
*G01R 33/48* (2006.01)
*G09B 19/00* (2006.01)
(Continued)

(52) U.S. Cl.
CPC ............ *A61B 5/0042* (2013.01); *A61B 5/055* (2013.01); *G01R 33/4806* (2013.01); *G06T 7/0014* (2013.01); *G09B 19/00* (2013.01); *G16H 30/20* (2018.01); *G16H 30/40* (2018.01); *G16H 50/20* (2018.01); *G16H 50/30* (2018.01); *G16H 50/70* (2018.01); *G16H 70/60* (2018.01); *A61B 2503/10* (2013.01); *A61B 2576/026* (2013.01);
(Continued)

(58) Field of Classification Search
None
See application file for complete search history.

(56) References Cited

U.S. PATENT DOCUMENTS

| 7,069,068 B1* | 6/2006 | Ostergaard ............ A61B 6/507 600/407 |
| 2010/0174171 A1 | 7/2010 | Lee et al. |
| 2019/0117700 A1* | 4/2019 | Honmou ............... A61K 9/0019 |

OTHER PUBLICATIONS

Extended European Search Report dated Sep. 16, 2021 in connection with European Application No. 18868370.0.
(Continued)

*Primary Examiner* — Idowu O Osifade
(74) *Attorney, Agent, or Firm* — Pierce Atwood, LLP

(57) ABSTRACT

Methods and apparatus for predicting performance of an individual on a task, the method comprises receiving brain imaging data for the individual, wherein the brain imaging data comprises structural brain data, determining values for at least one characteristic of the structural brain data within regions of interest defined for a population of individuals having different performance levels, and predicting based on the determined values, a performance potential of the individual.

20 Claims, 15 Drawing Sheets

(51) Int. Cl.
- *A61B 5/00* (2006.01)
- *G16H 70/60* (2018.01)
- *G16H 30/20* (2018.01)
- *G16H 50/30* (2018.01)
- *G16H 50/70* (2018.01)
- *G16H 50/20* (2018.01)
- *G16H 30/40* (2018.01)
- *A61B 5/055* (2006.01)
- *G06T 7/00* (2017.01)
- *G16H 20/30* (2018.01)

(52) U.S. Cl.
CPC ............... *G06T 2207/10088* (2013.01); *G06T 2207/30016* (2013.01); *G06T 2207/30104* (2013.01); *G16H 20/30* (2018.01)

(56) References Cited

OTHER PUBLICATIONS

PCT/IB2018/001307, Feb. 18, 2019, International Search Report and Written Opinion.
PCT/IB2018/001307, Apr. 30, 2020, International Preliminary Report on Patentability.
International Search Report and Written Opinion for International Application No. PCT/IB2018/001307, dated Feb. 18, 2019.
International Preliminary Report on Patentability for International Application No. PCT/IB2018/001307, dated Apr. 30, 2020.
Wang et al., Sparse Multi-Task Regression and Feature Selection to Identify Brain Imaging Predictors for Memory Performance. Proc IEEE International Conference on Computer Vision. 2011. pp. 557-562. 15 pages. Retrieved from the Internet: https://www.ncbi.nlm.nih.gov/pmc/articles/PMC4184284 [last accessed Jun. 8, 2020].

\* cited by examiner

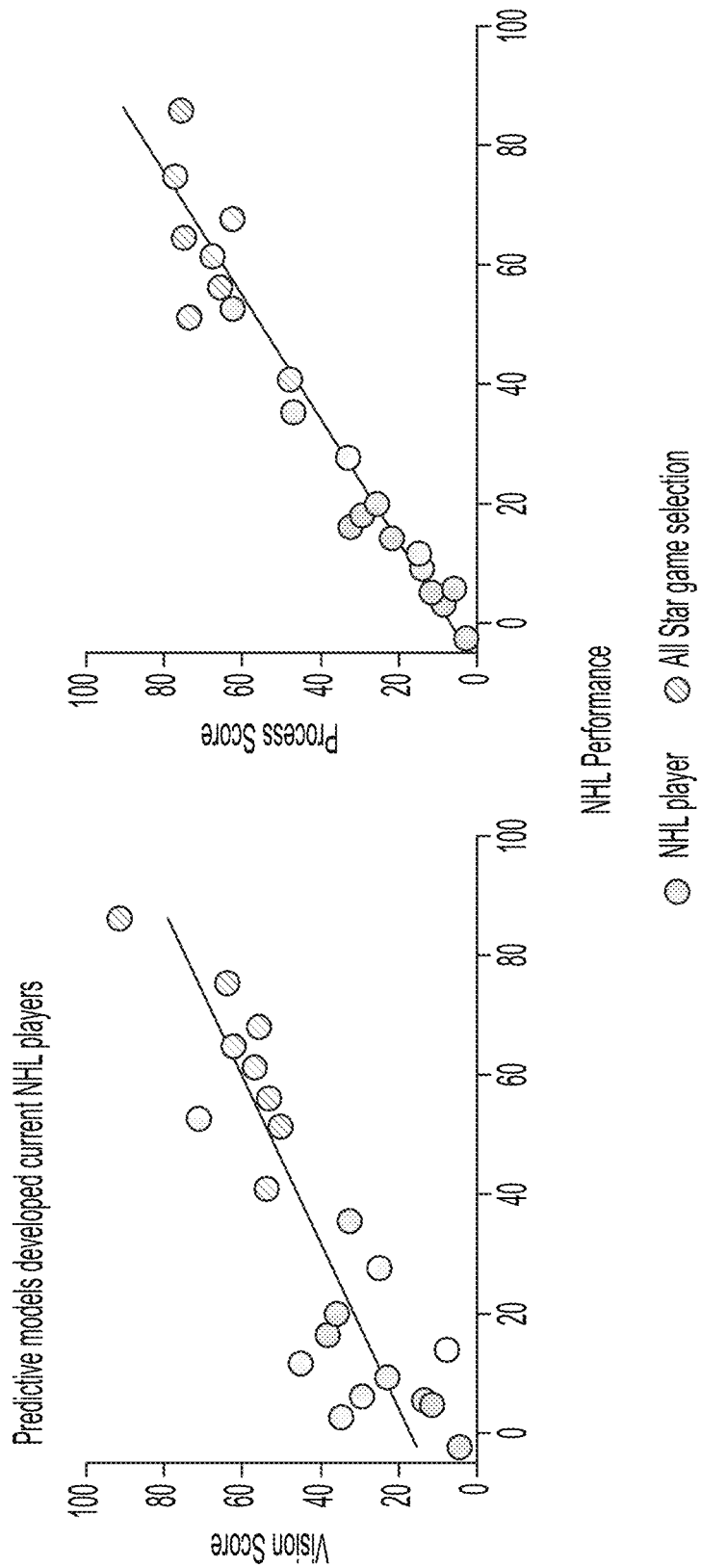
FIG. 11B1

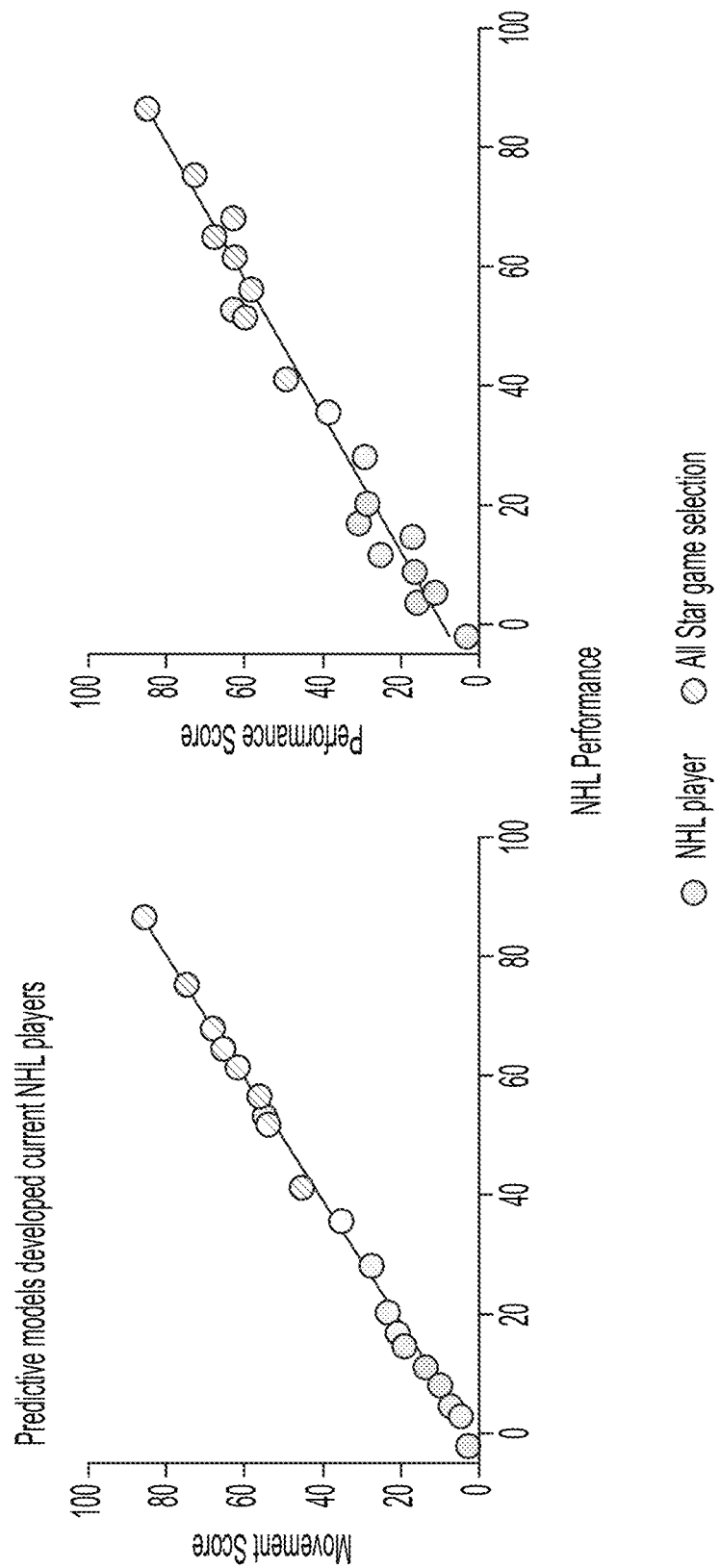
FIG. 11B2

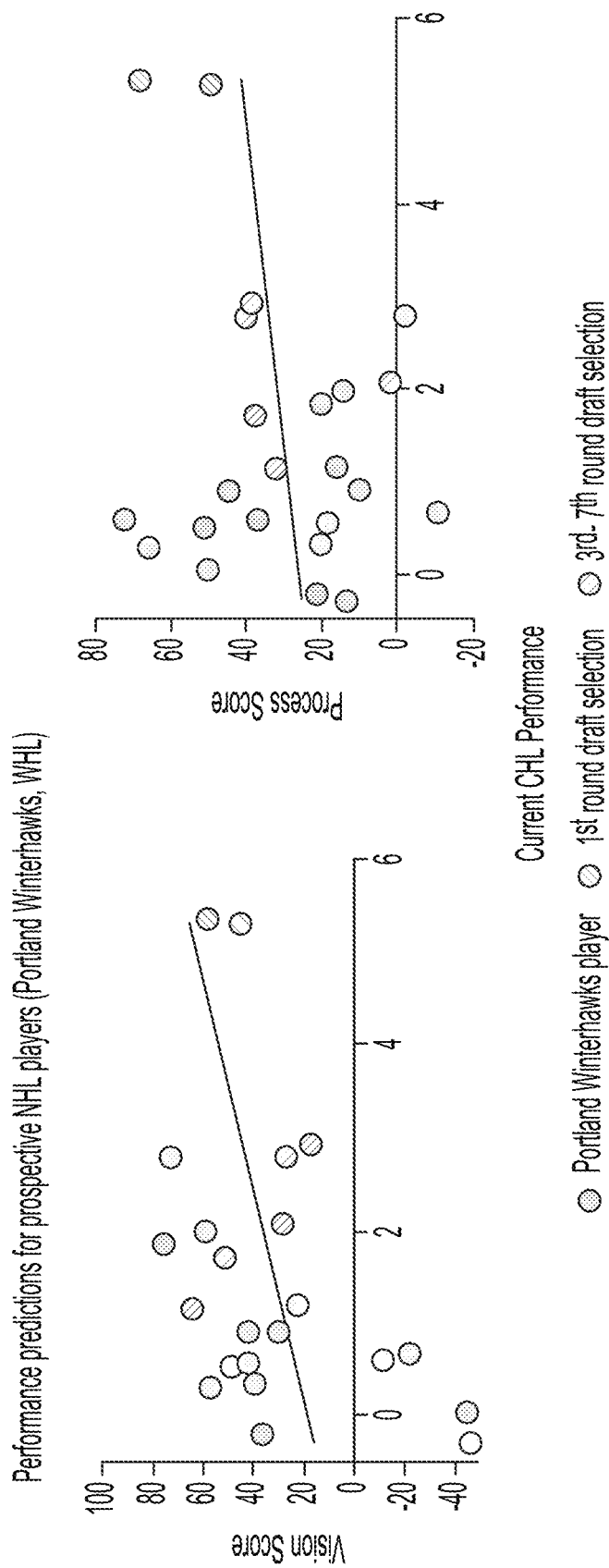
FIG. 11C1

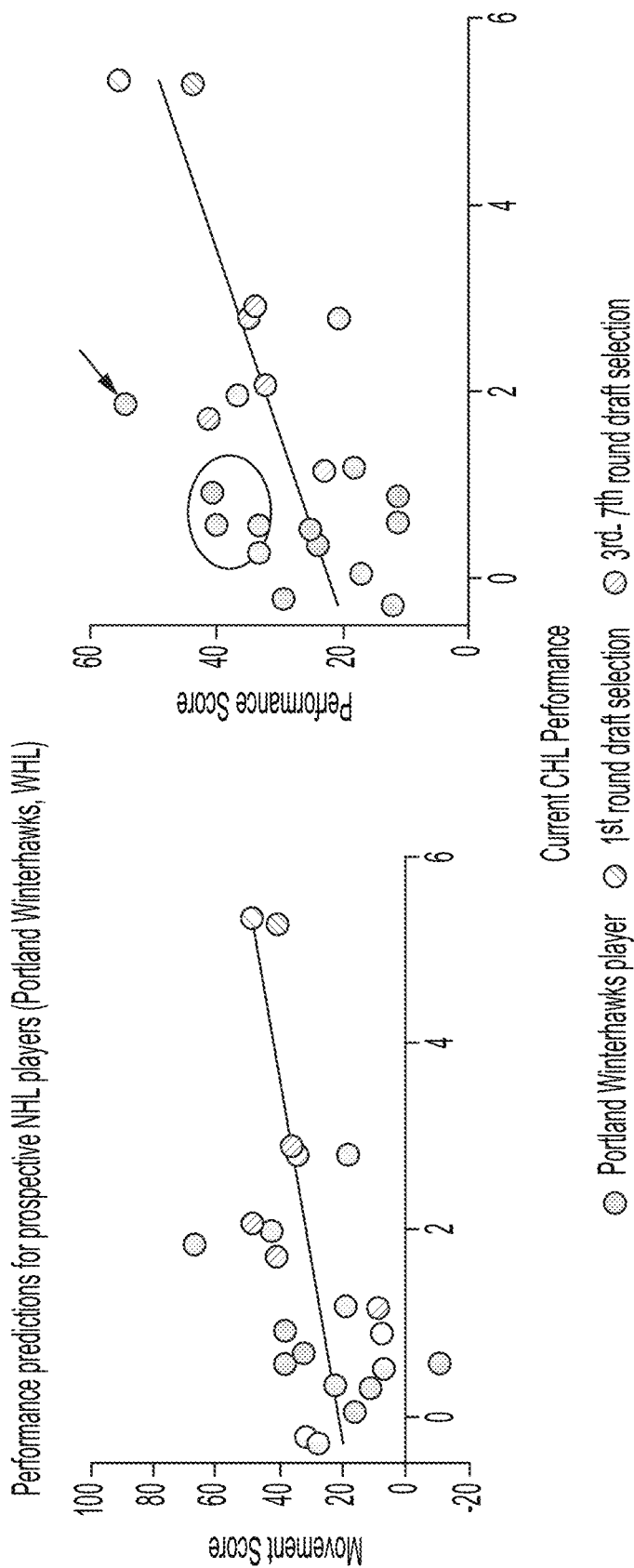
FIG. 11C2

METHODS AND APPARATUS FOR USING BRAIN IMAGING TO PREDICT PERFORMANCE

CROSS REFERENCE TO RELATED APPLICATIONS

This application is a national stage filing under 35 U.S.C. § 371 of international application number PCT/IB2018/001307, filed Oct. 16, 2018, which claims the benefit under 35 U.S.C. § 119(e) of U.S. Provisional Patent Application Ser. No. 62/573,027, filed Oct. 16, 2017, and entitled "METHODS AND APPARATUS FOR USING BRAIN IMAGING TO PREDICT PERFORMANCE," the entire contents of each of which is incorporated by reference herein.

BACKGROUND

Evaluation of a person's performance on a task is often based in part on qualitative observations of the person as he/she performs the task. For example, scouts often observe the play of college athletes when considering whether they would be successful performing on a professional sports team. Quantitative measurements, such as performance statistics are also often used to evaluate how well a particular person has performed a task. For example, statistics describing how well a particular investor's investment choices yielded positive returns for his/her client may be used to evaluate how skilled the investor is developing successful investment strategies.

SUMMARY

Some embodiments are directed to a computerized system for predicting performance. The system comprises at least one computer processor and at least one computer-readable medium encoded with a plurality of instructions that, when executed by the at least one computer processor, perform a method of predicting performance of an individual. The method comprises receiving brain imaging data for the individual, wherein the brain imaging data comprises structural brain data, determining first values for at least one characteristic of the structural brain data within regions of interest defined for a population of individuals having different performance levels, and predicting based, at least in part, on the first values, a performance potential of the individual.

Some embodiments are directed to a computer-implemented method for predicting performance. The method comprises receiving brain imaging data for the individual, wherein the brain imaging data comprises structural brain data, determining first values for at least one characteristic of the structural brain data within regions of interest defined for a population of individuals having different performance levels, and predicting, based on the first values, a performance potential of the individual.

Some embodiments are directed to a computerized system for identifying brain regions that predict differences in task performance. The system comprises at least one computer processor and at least one computer-readable medium encoded with a plurality of instructions that, when executed by the at least one computer processor, perform a method. The method comprises receiving brain imaging data for each of a plurality of individuals in a reference cohort, wherein the brain imaging data comprises structural brain data characterizing a static state of a brain and physiological brain data characterizing a dynamic state of the brain, receiving functional skill data for each of the plurality of individuals in the reference cohort, wherein the functional skill data indicates a performance score for each of the plurality of individuals on one or more tasks, determining, based, at least in part, on at least one first characteristic of the structural brain data, at least one second characteristic of the physiological brain data, and the functional skill data, brain regions associated with differences in performance on the one or more tasks, and outputting the determined brain regions as a set of predictive regions of interest.

Some embodiments are directed to a computer-implemented method for identifying brain regions that predict differences in task performance. The method comprises receiving brain imaging data for each of a plurality of individuals in a reference cohort, wherein the brain imaging data comprises structural brain data characterizing a static state of a brain and physiological brain data characterizing a dynamic state of the brain, receiving functional skill data for each of the plurality of individuals in the reference cohort, wherein the functional skill data indicates a performance score for each of the plurality of individuals on one or more tasks, determining, based, at least in part, on at least one first characteristic of the structural brain data, at least one second characteristic of the physiological brain data, and the functional skill data, brain regions associated with differences in performance on the one or more tasks, and outputting the determined brain regions as a set of predictive regions of interest.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF DRAWINGS

Various non-limiting embodiments of the technology will be described with reference to the following figures. It should be appreciated that the figures are not necessarily drawn to scale.

FIG. 11B1 and 11B2 show results of an example analysis for each component shown in FIG. 11A and overall potential demonstrating the correlation between neurological feature selection and athlete performance; and FIG. 11C1 and FIG. 11C2 are plots showing the same analysis used to generate the results for FIG. 11B1 and FIG. 11B2 as applied to prospective professional hockey players.

DETAILED DESCRIPTION

The inventors have recognized and appreciated that conventional qualitative and quantitative techniques for evaluating the performance of an individual to perform a particular task or set of tasks may be improved by considering physiological and neurological data that is not typically used to evaluate task performance. Additionally, conventional quantitative measures used to evaluate an individual's performance typically only consider how well the person performs the task by, for example, assigning them a score (e.g., the individual scored $^{20}/_{50}$ on the Wonderlic Personnel Test), without considering the individual's potential for performance on the task. To this end, some embodiments are directed to techniques for using brain imaging to estimate both an individual's potential for performance on one or more tasks and a current level of performance for the individual in performing the task. By estimating both potential and current performance, it is possible to assess whether the individual can be trained to improve performance (i.e., if there is room for improvement within their potential) or whether the individual is currently performing near their potential and does not have much room to improve through training. Based, at least in part, on a result of the analysis techniques described herein, individualized deficits can be identified for improvement and personalized training programs may be designed to improve an individual's performance within their potential level of performance.

The inventors have recognized and appreciated that one or more measures of brain structure may be used to assess performance potential and one or more measures of brain physiology may be used to assess current performance within an individual's potential. To this end, some embodiments are directed to using structural and physiological brain data to predict an individual's performance on a task using a classifier trained to associate brain data with performance metrics. Some embodiments are directed to techniques for developing predictive models of performance by training a model (e.g., a neural network) using brain imaging data extracted from a cohort of high performing and lower performing subjects, as discussed in more detail below. Applications of estimating the performance using brain data in accordance with the techniques described herein include, but are not limited to assessing athletic performance, military performance, executive performance, and financial analysis performance.

Figure 1:
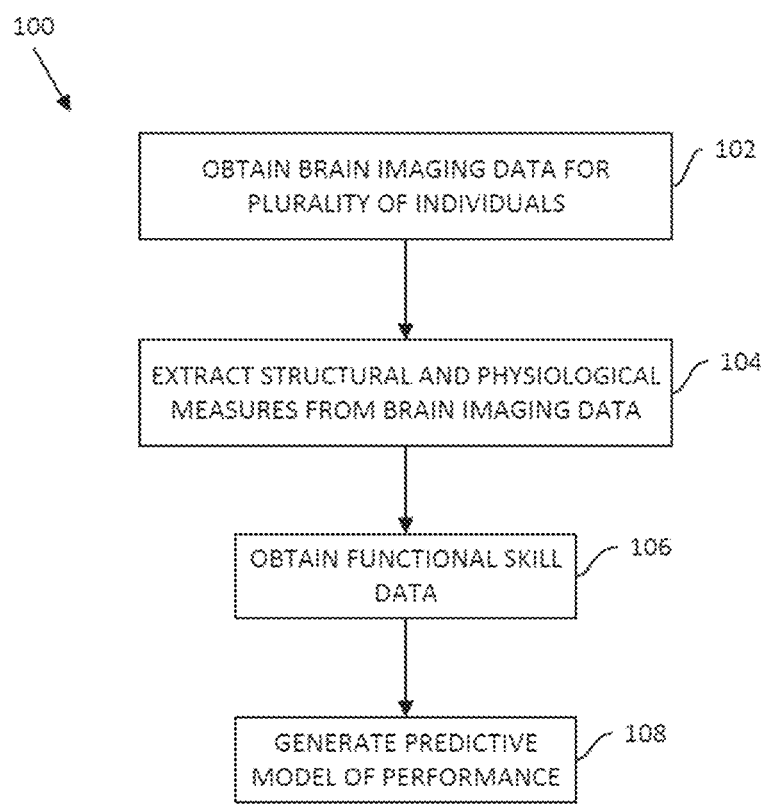
FIG. 1 is a flowchart of a process for generating a predictive model of performance in accordance with some embodiments.

FIG. 1 illustrates a process 100 for generating a predictive model of performance (e.g., a trained classifier) in accordance with some embodiments. In act 102, brain imaging data is acquired from a plurality of individuals having different skill levels. For example, the plurality of individuals may include a group of elite athletes (e.g., Olympic-level athletes, professional athlete all-stars) and a group of individuals who are not elite athletes (e.g., non-athletes, casual athletes).

Figure 2:
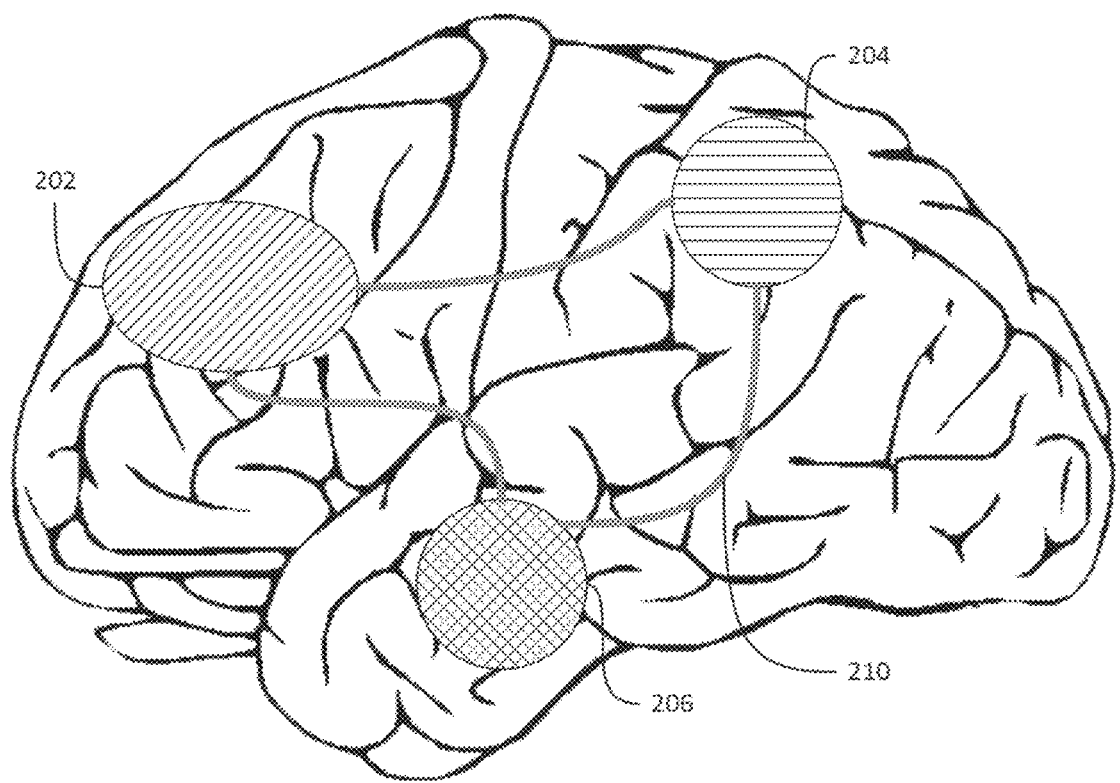
FIG. 2 is a schematic of a brain including a structural functional unit in accordance with some embodiments.

In some embodiments, the obtained brain imaging data includes structural brain data and physiological brain data associated with a "structural-functional unit" (SFU) that represents a functional network of connected nodes in the brain that are activated together to perform various cognitive, sensory, motor, or sensorimotor tasks. Examples of SFUs include, but are not limited to, a visuospatial network, a sensorimotor network, a default mode network, a working memory network, a salience network, an executive control network, a language network, and a motivation reward network. FIG. 2 schematically illustrates the concept of an SFU that includes a plurality of gray matter regions of the brain and white matter tracts connecting the gray matter regions. For example, the illustrative SFU shown in FIG. 2, includes three gray matter regions 202, 204 and 206 and white matter tracts (e.g., white matter tract 210) connecting the gray matter regions. Although shown as relatively large regions for illustration, it should be appreciated that the gray matter regions included in an SFU may be any size or shape. Additionally, although the white matter tracts in the illustrated SFU are shown as single lines connecting the gray matter regions, it should be appreciated that any suitable number of white matter tracts may connect gray matter regions in an SFU, and embodiments are not limited in this respect. SFUs may be defined, for example, based on the scientific literature, functional neuroimaging, or in any other suitable way.

In some embodiments, the structural brain data and physiological brain data are acquired using magnetic resonance imaging (MRI). It should be appreciated, however, that in other embodiments one or both of the structural brain data and physiological brain data may be acquired using a brain imaging technique other than MRI including, but not limited to, computed tomography (CT), positron emission tomography (PET) and optical imaging (e.g., optical coherence tomography OCT)). Additionally, multiple scans using different imaging parameters (e.g., to achieve different contrasts) or experimental conditions (e.g., different tasks) may be used to obtain the structural brain data and/or the physiological brain data.

In some embodiments, the structural brain data includes multiple types of structural brain data including, but not limited, to structural white matter connectivity data (e.g., obtained using diffusion tensor imaging (DTI)), white matter volume data, and gray matter volume data. One or more of the types of structural brain data may further include particular metrics used to characterize regions of the brain. For example, diffusion tensor imaging data may be used to evaluate for a voxel or group of voxels, one or more of fractional anisotropy (FA), mean diffusivity (MD), axial diffusivity (AD) and radial diffusivity (RD). The structural brain data may characterize a static state of the brain in that the structural connections do not change during performance of a task.

In some embodiments, the physiological brain data includes multiple types of physiological brain data including, but not limited to, functional neuroimaging data (e.g., to assess resting state functional connectivity), cerebral blood flow data, cerebral vascular reactivity data, electroencephalography, function near infrared spectroscopy, near infrared spectroscopy, magnetoencephalography, computed tomography perfusion, transcranial Doppler, positron emission tomography and single photon emission computed tomography. In some embodiments, at least some of the physiological brain data may characterize a blood oxygen level dependent (BOLD) response within different regions of the brain (e.g., voxel or group of voxels) over time. In such a way, the physiological brain data captures dynamics of the brain in contrast to the structural brain data, described above.

Brain data obtained from a plurality of individuals may be transformed into common brain space representation for analysis. For example, the obtained brain data may be transformed into the standardized Montreal Neurological Institute (MNI) brain coordinate space or the data may be transformed into another brain space representation (e.g., a brain space template defined by acquired brain data) that facilitates analysis in a common brain space. Additionally, at least some of the obtained brain data may be transformed to have a same voxel size. For example, brain data of a first type may be downsampled (or upsampled) to have a spatial resolution corresponding to brain data of a second type within the common brain space.

Returning to process 100, after the brain imaging data is obtained, the process proceeds to act 104, where at least one structural measure is extracted from the structural brain data and at least one physiological measure is extracted from the physiological brain data. Examples of extracting structural measures and physiological measures from obtained brain data are described in more detail below. Process 100 then proceeds to act 106 where functional skill data is obtained from the plurality of individuals from whom the brain imaging data was obtained in act 102. The functional skill data may be obtained, for example, by presenting the plurality of individuals with a set of standardized tasks and recording responses to the performance of the tasks. Process 100 then proceeds to act 108, where a predictive model of performance is generated based, at least in part, on the obtained functional skill data and the structural and physiological measures extracted from the brain imaging data. As discussed in more detail below, in some embodiments, the predictive model is a classifier (e.g., a neural network) having parameters determined based on the functional skill data, the structural brain measures, and/or the physiological brain measures. In some embodiments, the predictive model may be generated based on multiple predictive models, each of which is generated for predicting performance on one or more particular tasks or sub-tasks, examples of which are described in more detail below.

Figure 3:
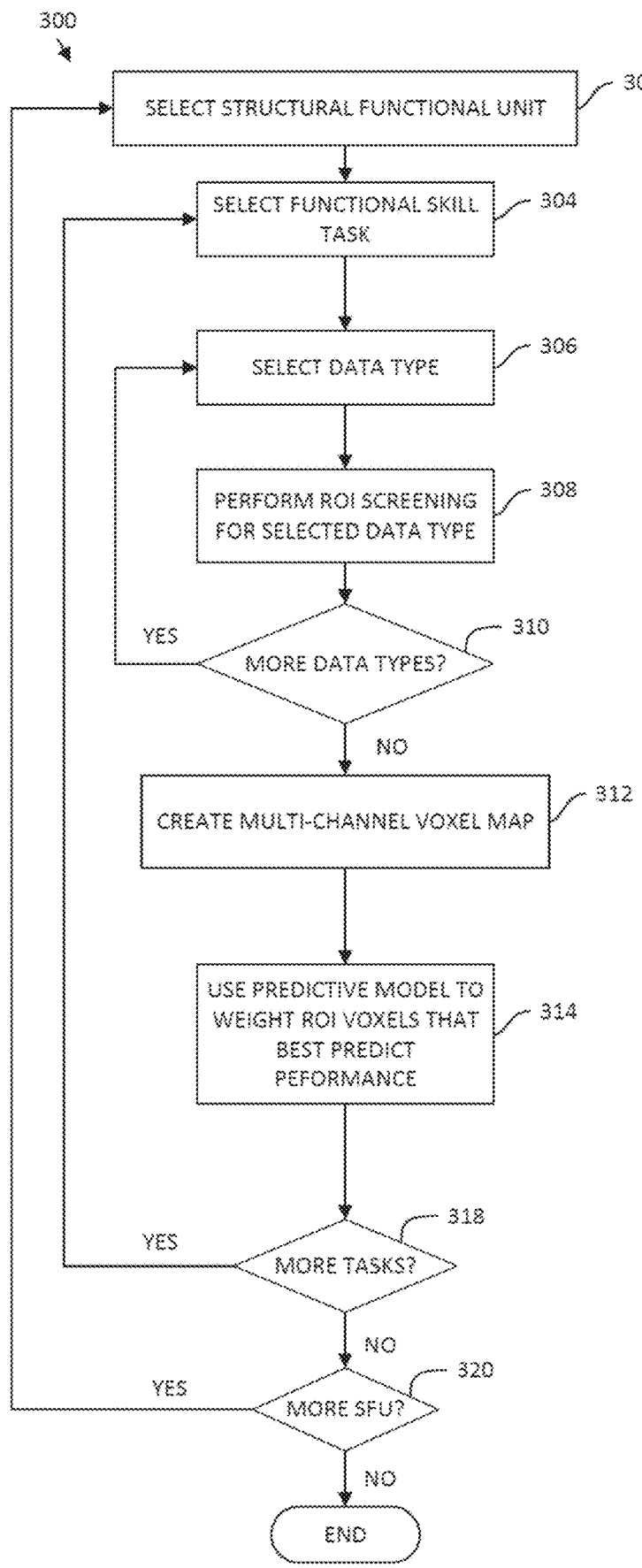
FIG. 3 is a flowchart of a process for generating a predictive model that includes multiple brain imaging data types in accordance with some embodiments.

FIG. 3 illustrates a process 300 for analyzing obtained brain imaging data to extract structural and physiological brain measures used to generate one or more models for predicting performance in accordance with some embodiments. In act 302, a structural functional unit (SFU) is selected for analysis. Rather than analyzing every voxel in the obtained brain imaging data volume, the selected SFU is used to constrain the analysis in process 300 to voxels represented within the gray matter nodes and/or white matter tracts connecting the gray matter nodes of the SFU.

Process 300 then proceeds to act 304 where a functional skill task or sub-task is selected for analysis. As discussed above in connection with act 106 of process 100, each of the plurality of individuals included in a reference cohort perform a plurality of functional skill tasks to obtain function skill data. In some embodiments, each of the individuals in the reference cohort performs a battery of standardized tests (e.g., the KINARM Standard Tests available from BKIN Products, Kingston, Ontario, Canada), and scores representing the individual's performance on each of the tests are determined and recorded. Some of the standardized tests may include multiple sub-tasks or metrics that capture different aspects of the individual's performance during the tests. Rather than selecting a particular standardized test in act 304, one of the sub-tasks or metrics included in a test may instead be selected.

Process 300 then proceeds to act 306, where a particular data type from the obtained brain imaging data is selected. As discussed above, the brain imaging data may include structural brain data and physiological data, each of which may also comprise multiple data types. As an example, the structural brain data may include structural brain data obtained using diffusion tensor imaging, gray matter volume data, and white matter volume data, each corresponding to a different data type that may be selected in act 306. Similarly, the physiological data may include multiple data types each of which may be selected for analysis in act 306.

Process 300 then proceeds to act 308, where region of interest (ROI) screening is performed for the selected data type, structural functional unit, and task or sub-task or metric. The objective of the ROI screening is to identify regions of the brain included in the selected SFU that characterize differences in performance on the selected task, sub-task, or metric. The output of the ROI screening process in act 308 is a set of brain regions (e.g., voxels or groups of voxels) and associated values representing a prediction strength describing how strongly the voxels in each brain region are predictive of strong vs. poor performance on the selected task, sub-task or metric. An example of performing ROI screening in accordance with some embodiments is discussed in more detail with regard to FIG. 4.

Process 300 then proceeds to act 310, where it is determined whether there are additional data types to analyze. If it is determined in act 310 that there are additional data types to analyze, process 300 returns to act 306, where a new data type is selected and the ROI screening process in act 308 is repeated for the new data type. The resulting ROI screening process being a new set of brain regions within the SFU and associated values within each brain region for the selected brain data type that differentiate strong vs. poor performance on the selected task, sub-task, or metric. The process of acts 306-308 repeats until it is determined in act 310 that there are no other data types to analyze.

When it is determined in act 310 that there are no other data types to analyze, process 300 proceeds to act 312, where a multi-channel voxel map is created based on the output of the ROI screening process at each iteration of act 308 that is performed in process 300. As described above, a structural functional unit defines a set of brain regions (e.g., gray matter regions) and connections (e.g., white matter tracts) between the brain regions. Within the brain regions defined by the SFU, each iteration through acts 306-308 results in a subset of those regions in the SFU being identified as predictive of strong vs. poor performance differences on a task, sub-task, or metric. Accordingly, the output of the ROI screening process in act 308 is a spatial map of brain regions within the SFU that characterize the differential task/sub-task/metric performance for a particular data type. For example, if the data types include structural connectivity, resting state functional connectivity, and cerebral blood flow, the output of the ROI screening process in act 308 would be a map for each of these data types. Conceptualized another way, each voxel within the SFU may be associated with multiple "channels," where each channel represents a different data type. Continuing with the example above, each voxel in the SFU may be associated with a tuple of channels—(structural connectivity, resting state functional connectivity, cerebral blood flow). As described in more detail below, the values ascribed to each channel for each voxel may be determined using a predictive model (e.g., a neural network) that reflects the strength of that voxel for predicting differences between strong and weak performers using the particular data type associated with the channel. The resultant map created in act 312 is then a spatial map of voxels in an SFU, where each of the voxels is associated with multiple channels for the different data types. In some embodiments, a visualization of the created multi-channel voxel map may be created and displayed (e.g., by using a color space (e.g., RGB, CMYK) to represent the different channels for each voxel.

After creating a multi-channel voxel map for a particular SFU and task, sub-task, or metric, process 300 proceeds to act 314, where a predictive model is used to weight the voxels within each identified ROI, such that the value for each channel in the multi-channel voxel map reflects the strength of that voxel for predicting differences between strong and weak performers using the particular data type associated with the channel trained based on the values in the multi-channel voxel map. Examples of predictive models that may be used in accordance with some embodiments include, but are not limited to neural networks (e.g., convolutional neural networks), support vector machines, and random forest classifiers. In one embodiments, a convolutional neural network regression analysis may be used to weight the ROI voxels that best predict task performance.

Process 300 then proceeds to act 318, where it is determined whether there are more tasks, sub-tasks, or metrics to analyze. If it is determined in act 318 that there are additional tasks, sub-tasks, or metrics to analyze, process 300 returns to act 304. For example, if one of the standardized tests included ten different individual metrics, acts 304-316 may be performed for each of the ten different individual metrics, resulting in ten different predictive models of performance for the corresponding metrics. When it is determined in act 318 that all tasks, sub-tasks, or metrics have been analyzed, process 300 proceeds to act 320, where it is determined whether there are additional SFUs to analyze. If it is determined in act 320 that there are additional SFUs to analyze, process 300 returns to act 302, where a new SFU is selected, and acts 302-318 repeat until it is determined in act 320 that all SFUs have been analyzed, with the resultant output of process 300 being a plurality of predictive models of performance for each of a plurality of structural functional units. The predictive models of performance may be combined in any suitable way into a combined predictive model for performance that may be used to predict performance for a new individual not included in the reference cohort.

Figure 4:
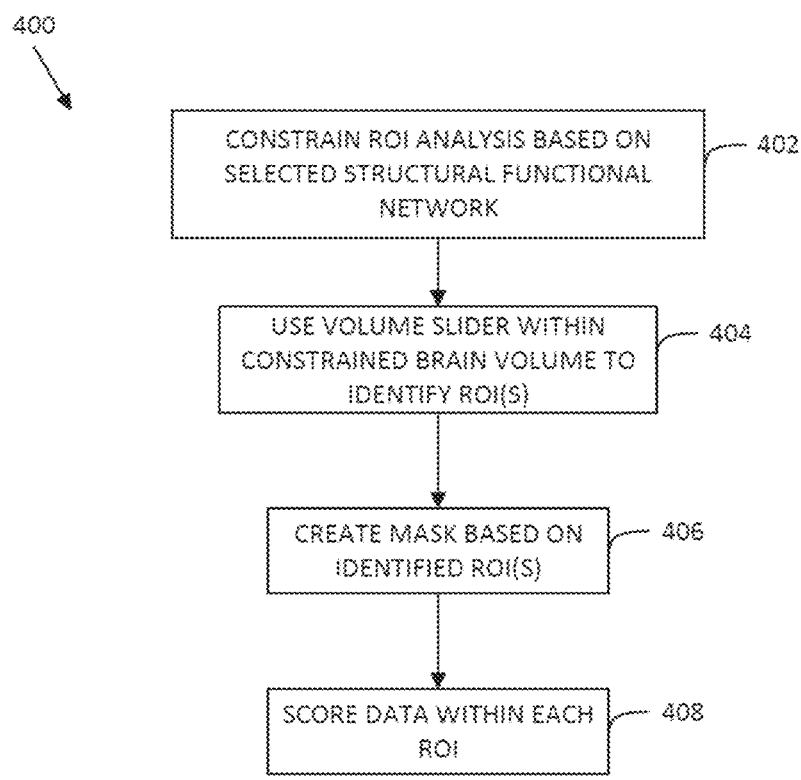
FIG. 4 is a flowchart of a process for performing region of interest screening in accordance with some embodiments.

FIG. 4 illustrates a process 400 for performing ROI screening in accordance with some embodiments. In act 402, the ROI analysis is constrained based on the selected structural functional network being analyzed. As discussed above, each time that the ROI screening is performed, only voxels within brain regions included in a particular SFU are considered. Process 400 then proceeds to act 404, where a volume slider is used to identify ROIs within the SFU that reflect differences in performance on a task, sub-task or metric as described above. The volume slider comprises a group of contiguous pixels over which a local transformation is performed to obtain a value (e.g., an average value) for the slider volume. For example, if the volume slider is a 3×3×3 cube that includes 27 pixels, an average value across the 27 pixels in the volume slider may be calculated and assigned to the voxel in the center of volume slider. The volume slider may then slide to a new position within the SFU and a new value for the volume slider may be calculated. Using a volume slider in accordance with some embodiments accommodates registration errors when individual brain data is registered to a standard brain space (e.g., the Montreal Neurological Institute (MNI) standard brain) and also accounts for variability in brain anatomy between individuals. Although the example above describes using a cube-shaped volume slider having 3×3×3 pixels, it should be appreciated that other size and shape volume sliders may alternatively be used, and embodiments are not limited in this respect.

In some embodiments, the volume slider is used to determine an average value for each voxel (or sub-volume) within an SFU for each individual in the reference cohort. To determine how each voxel is predictive of performance on a selected task, sub-task or metric, a voxel-by-voxel numerical comparison (e.g., using a Student's t-test) is made between values for a first group of subjects that performed well on the task/sub-task/metric (e.g., the top 20% performers) and values for a second group of subjects that performed poorly on the task/sub-task/metric (e.g., the bottom 20% performers) to identify ROIs that are predictive of the task/sub-task/metric performance differences. For example, the ROIs may be identified by thresholding the values of the numerical comparison to omit those voxels (or sub-volumes) that are less than a threshold value.

Process 400 then proceeds to act 406, where a mask is created based on the identified ROIs that characterize the performance differences. Process 400 then proceeds to act 408 where data within each ROI is scored to produce the resultant spatial map for the particular data type, SFU, and task/sub-task/metric.

Figure 5:
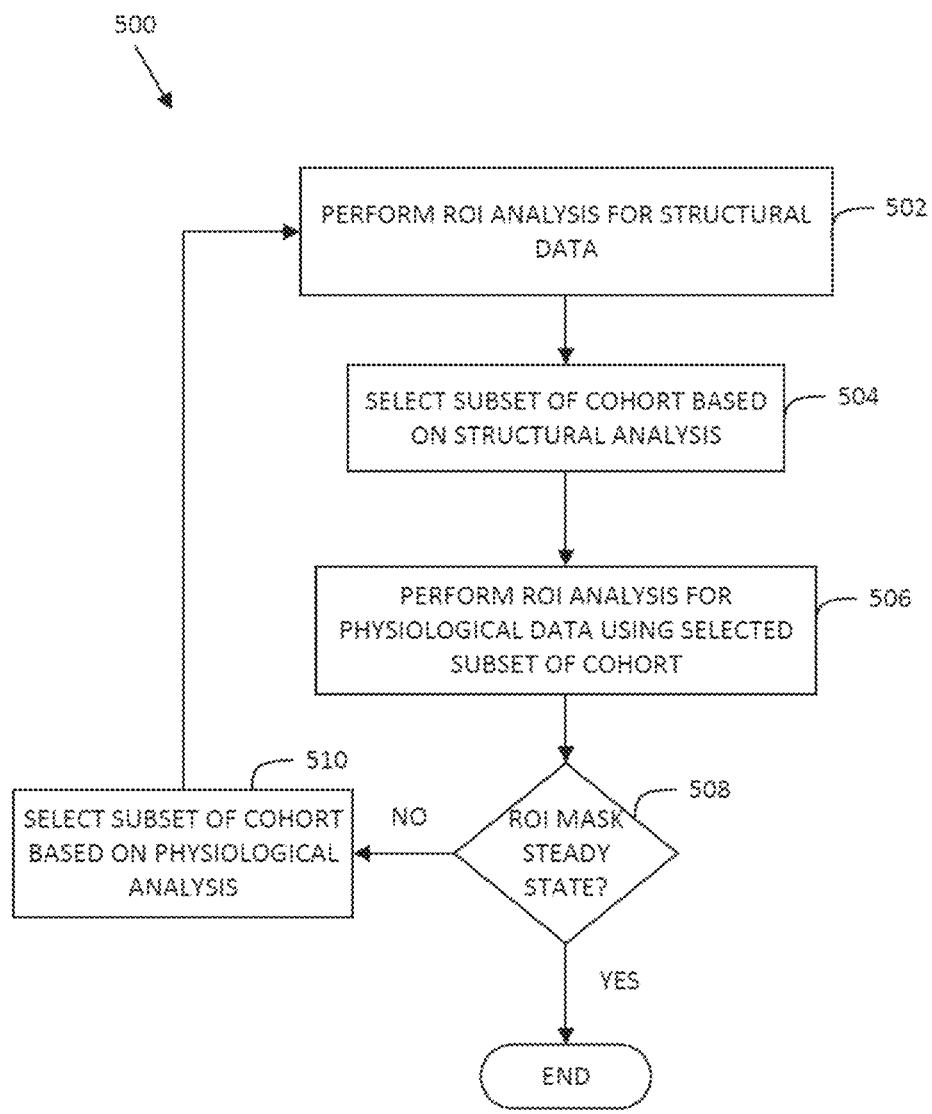
FIG. 5 is a flowchart of a process for iteratively identifying a set of regions of interest in accordance with some embodiments.

The inventors have recognized that when identifying ROIs by analyzing brain imaging data that includes structural brain data and physiological brain data, it may be advantageous to iteratively refine the ROIs identified for a particular task by holding either structure constant or physiology constant while varying the other variable. FIG. 5 illustrates a process 500 for iteratively identifying ROIs for a particular task in accordance with some embodiments. In act 502, an ROI screening process is performed for each of multiple sets of structural brain data types (e.g., DTI data, gray matter volume). The scores for the multiple sets of structural brain data may then be combined. For example, the scores can be averaged or the scores may be combined in some other manner (e.g., a weighted average). Process 500 then proceeds to act 504, where a subset of the individuals in the reference cohort are selected based on the ROI analysis of the structural data. For example, all individuals in the reference cohort may be ranked according to a measure of "structural quality," and the top 50% of structural scoring subjects may be selected in act 504. Process 500 then proceeds to act 506, where an ROI screening process is performed for each of multiple sets of physiological brain data types (e.g., cerebral blood flow, resting state functional connectivity), as discussed above in connection with FIG. 4. Process 500 then proceeds to act 508 where it is determined whether the identified ROI masks output from act 506 are similar enough to the ROI masks output from act 502. Any suitable measure of similarity may be used to determine whether the ROI masks have reached "steady state" in act 508. If it is determined in act 508 that steady state of the output ROI masks has not been achieved, process 500 proceeds to act 510, where a subset of the individuals in the reference cohort are selected based, at least in part, on their physiological scores. For example, the top 50% of physiological scoring subjects may be selected in act 510. Process 500 then returns to act 502, where an ROI screening process for structural brain data is performed on the subset of the individuals in the reference cohort (e.g., the top 50% physiological scoring subjects output from act 506). Process 500 continues until it is determined in act 508 that the ROI mask output from the ROI screening process has reached a steady state.

The inventors have recognized and appreciated that structural brain data (e.g., white matter organization in white matter tracts within an SFU), which reflects a static state of the brain, may be used to determine an individual's capacity, ceiling, or "potential" with respect to task performance, and that physiological brain data (e.g., cerebral blood flow), which reflects dynamics of the brain, may be used to determine a current performance level within the performance range established by the structural brain data analysis of performance potential. Differences between the performance potential and the current performance level may be referred to as a performance "deficit," which represents a degree to which training the individual is likely to be effective in improving task performance up to the individual's measured potential. One or more predictive models generated in accordance with the techniques described herein may be used to predict a new individual's potential performance and current performance level relative to the potential performance level. To the extent that there is a difference between the individual's current performance level and potential performance level, a personalized training recommendation may be made to enable the individual to increase their current performance level to a level closer to their potential performance level by reducing their performance deficit.

Figure 6:
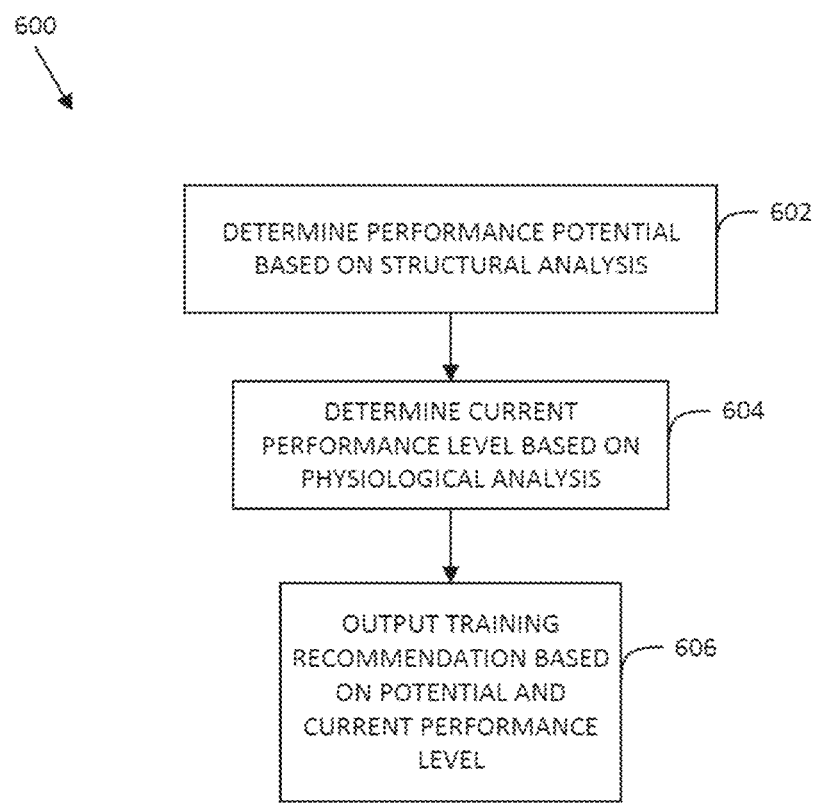
FIG. 6 is a flowchart of a process for predicting performance based on an analysis of structural and physiological brain data in accordance with some embodiments.

FIG. 6 illustrates a process 600 for determining a personalized training recommendation for an individual in accordance with some embodiments. In act 602, brain imaging data that includes structural data (e.g., DTI data) is obtained for an individual. The obtained brain imaging data may be transformed into a standard brain space (e.g., MNI coordinate space) and the ROI mask(s) determined based on the individuals in the reference cohort may be used to analyze the structural data. For example, within each of the ROIs defined by the ROI mask(s) values or scores (e.g., Z-scores) may be determined, and the scores may be used to determine a performance potential of the individual based on an analysis of the individual's structural data within the ROIs. Having established the individual's performance potential by analyzing the obtained structural data, process 600 proceeds to act 604, where physiological brain data (e.g., cerebral blood flow) obtained from the individual is used to determine the individual's current performance level by, for example, analyzing the physiological brain data within the ROIs defined by the ROI mask(s) determined based on the individuals in the reference cohort. After determining the individual's current performance level, process 600 proceeds to act 606, where a training recommendation is output based, at least in part, on the determined performance potential and current performance level. For example, a training recommendation may be made based, at least in part, on imbalances in structure, physiology, or both, and/or inefficiencies, for example, as detected in the individual's physiology relative to normalized control data.

In some embodiments, separate predictive models are generated and subsequently used to analyze structural brain data and physiological brain data acquired from an individual to predict performance. In other embodiments, a single predictive model that takes as input both structural measures determined from structural brain data and physiological measures determined from physiological brain data, is used to predict one or more performance measures for an individual.

Figure 7:
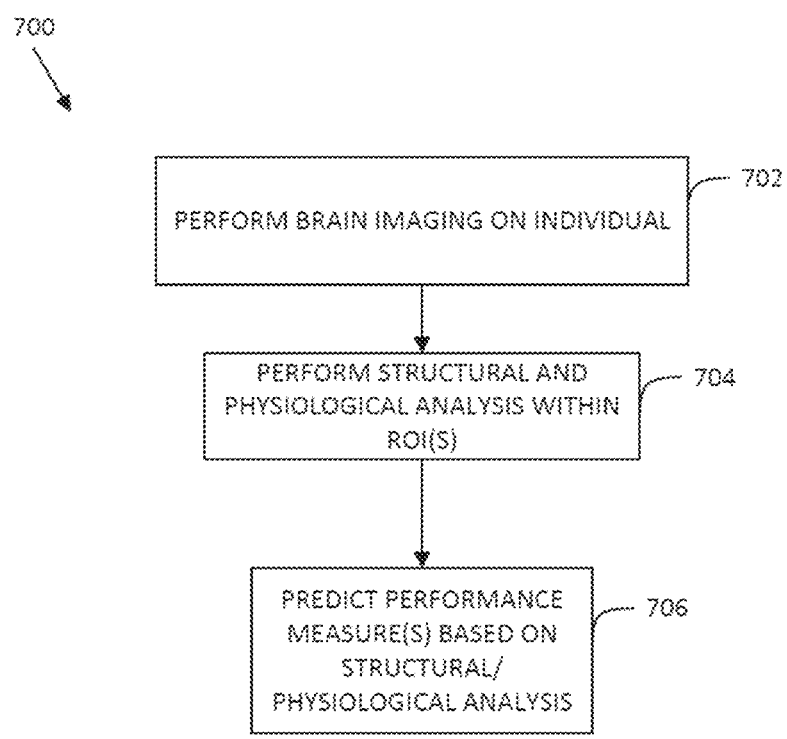
FIG. 7 is a flowchart of a process for predicting performance based on an analysis of structural and physiological brain data within regions of interest in accordance with some embodiments.

FIG. 7 illustrates a process 700 within which a single predictive model is used. In act 702, brain imaging is performed on the individual, wherein the brain imaging includes at least one structural scan to obtain structural brain data and/or at least one physiological scan to obtain physiological brain data. Process 700 then proceeds to act 704, where structural and physiological analyses are performed on the obtained structural and physiological brain data. For example, ROIs defined by analyzing the reference cohort of individuals, which represent brain regions within which differences between strong and weak performers were identified may be used to analyze the obtained structural and physiological brain data. The output of the ROI analysis may be a set of values or scores. Alternatively, the output of the ROI analysis may be a set of features that characterize the structural and physiological brain imaging data. Process 700 then proceeds to act 706, where one or more performance measures are predicted based, at least in part, on the structural and/or physiological analysis output from act 704. In some embodiments the predicted performance may be a classification of the individual into one of multiple performance groups (e.g., strong performer, average performer, poor performer). In other embodiments the predicted performance may be represented by one or more numerical values (e.g., on a scale of 0-100) that represent the predicted performance measures.

Figure 8:
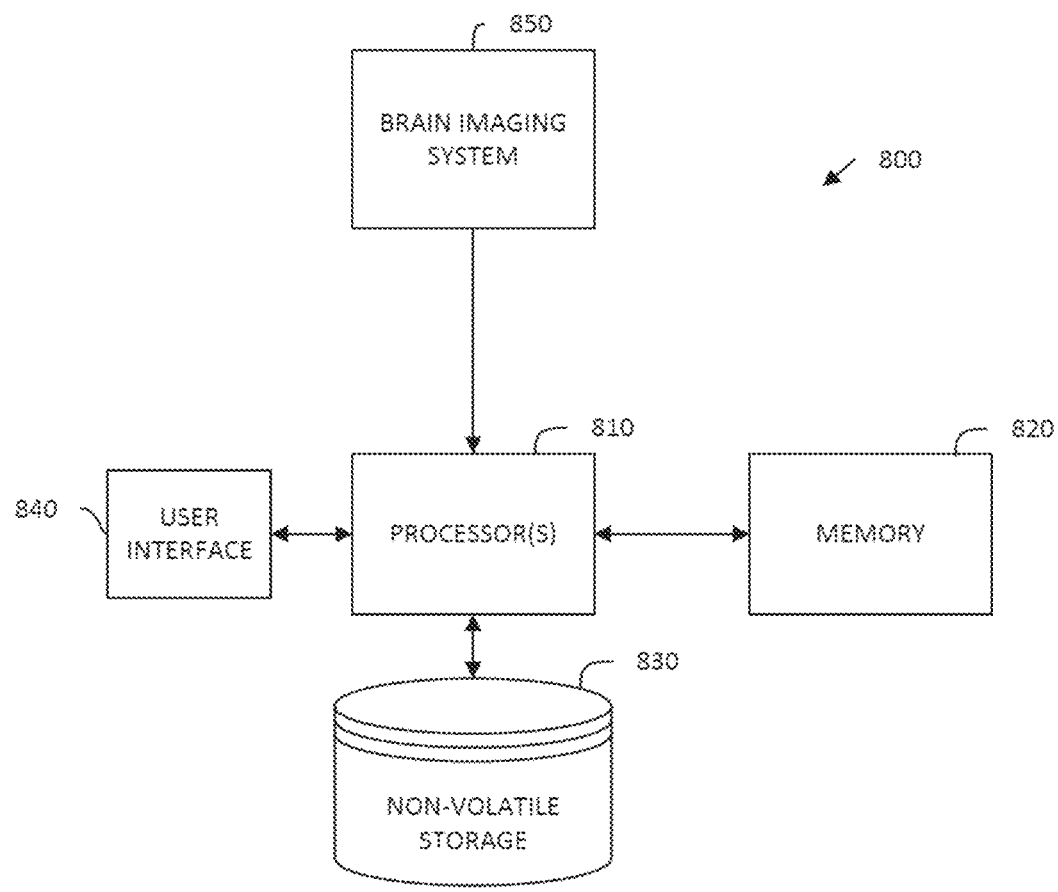
FIG. 8 is a block diagram of a computer system on which some embodiments may be implemented.

An illustrative implementation of a computer system 800 that may be used in connection with any of the embodiments of the disclosure provided herein is shown in FIG. 8. The computer system 800 includes one or more computer hardware processors 810 and one or more articles of manufacture that comprise non-transitory computer-readable storage media (e.g., memory 820 and one or more non-volatile storage devices 830). The processor(s) 810 may control writing data to and reading data from the memory 820 and the non-volatile storage device(s) 830 in any suitable manner. To perform any of the functionality described herein, the processor(s) 810 may execute one or more processor-executable instructions stored in one or more non-transitory computer-readable storage media (e.g., the memory 820), which may serve as non-transitory computer-readable storage media storing processor-executable instructions for execution by the processor(s) 810.

In some embodiments, computer system 800 also includes a brain imaging system (e.g., an MRI system) 850 that provides brain imaging data to processor(s) 810. Brain imaging system 850 may be communicatively coupled to processor(s) 810 using one or more wired or wireless communication networks. In some embodiments, processor(s) 810 may be integrated with the brain imaging system in an integrated device. For example, processor(s) 810 may be implemented on a chip arranged within a device that also includes brain imaging system 850.

Brain imaging system 850 may be configured to perform brain imaging on an individual to obtain structural brain data and physiological brain data. For example, the brain imaging system may be a magnetic resonance imaging system configured to acquire structural data from the individual using one more structural imaging scans and physiological data from the individual using one more functional imaging scans. The brain imaging data determined from the brain imaging system 850 may then be provided to the processor(s) 810 for inclusion in a performance prediction analysis, as described above.

In some embodiments, computer system 800 also includes a user interface 840 in communication with processor(s) 810. The user interface 800 may be configured to provide a training recommendation to a healthcare professional based, at least in part, on the results of performance prediction analysis output from processor(s) 810.

Illustrative Example

Figure 9:
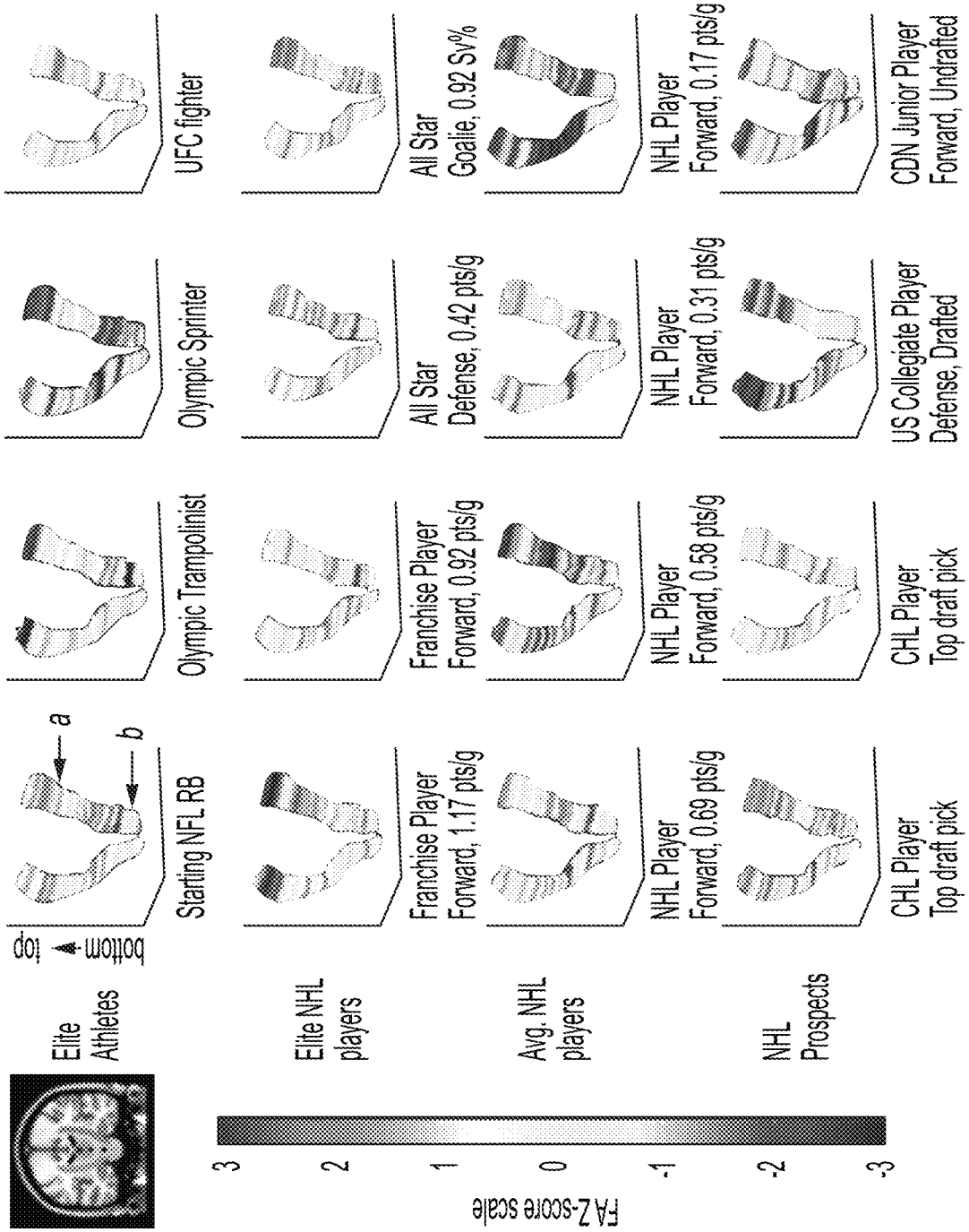
FIG. 9 is a plot showing examples of corticospinal tracts in a variety of athletes.

In this example, the left and right corticospinal tracts of several high performing elite athletes were examined. The corticospinal tract is a white matter tract that has a clear connection with athletics, as it comprises the primary bundle of axons that transmits neural signals developed in the primary motor cortex to the spinal cord and out to skeletal muscles through the peripheral nervous system. As a first step, fractional anisotropy (FA) values obtained from DTI scans of the left and right corticospinal tracts were examined. From a visual inspection it was possible to observe some distinct patterns. Highly elite athletes showed a very high FA values in their centrum semiovale as shown in FIG. 9. The centrum semiovale is a brain region involved in coordinating multiple inputs from various areas of the motor cortex. High FA values were also observed in the cerebral peduncle, the site where several motor fibres exit the corticospinal tract. This pattern was also notable because elite athletes also displayed a higher degree of symmetry between the left and right tract than non-elite athletes and the greatest FA values were found in the tract associated with their dominant hand or dominant style of play.

Figure 10:
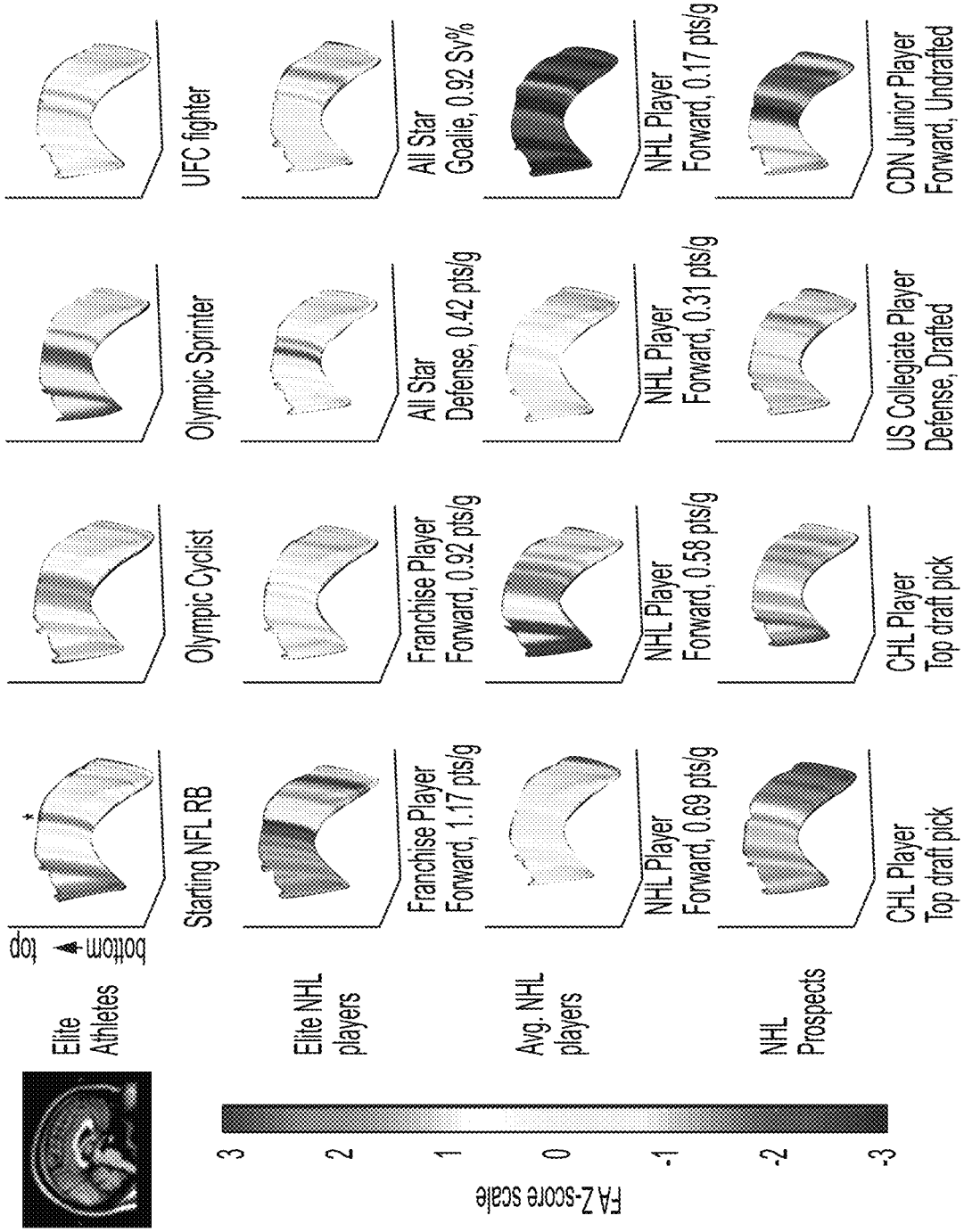
FIG. 10 is a plot showing examples of corpus callosum in a variety of athletes.

Based on these initial observations, ten brain regions and functional networks were selected to evaluate. The ten brain regions and functional networks were organized based on the principle that the primary components of athletic performance involve an athlete's ability to see a situation (Vision/See), determine a course of action (Process) and react based on that decision (Movement/Move). A total of 442 data points were extracted from the various brain regions. Examples of the average FA values extracted across 2 mm slices of the corpus callosum (a brain region for Process) can been see in FIG. 10. Interestingly, a distinct high FA band in the central posterior region of corpus callosum, known as the body, which was present more often in high performing elite athletes. This region includes the callosal motor and callosal premotor fibres that are involved in motor planning, execution and coordination. The premotor fibres are also connected to association networks in the parietal networks and play an important role of self-awareness in space.

Figure 11A:
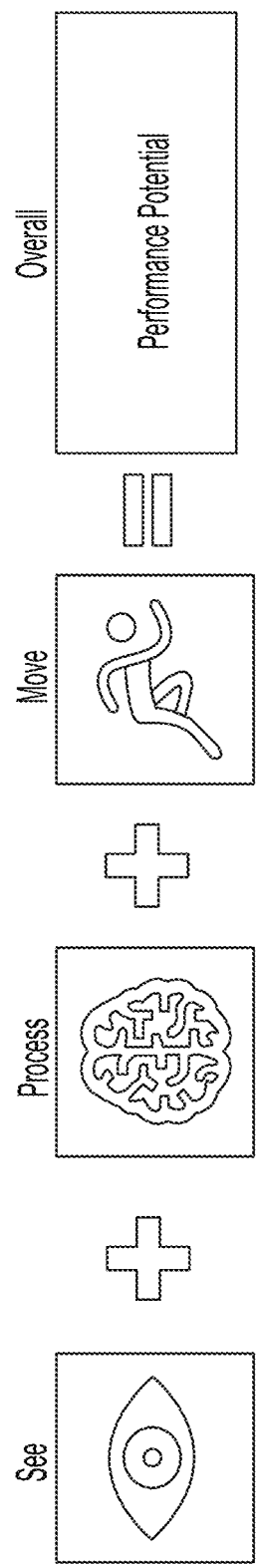
FIG. 11A schematically illustrates how the brain regions were defined to represent basic components of athletic performance that combine for overall performance in accordance with some embodiments.

To predict athletic potential from the data extracted from the MRI scans of current NHL players, a set of algorithmic predictive models were generated for each aspect of performance in accordance with the techniques described above. To define each algorithm, a dataset in which players' MRI data for the individual brain regions was selected and compared against the players' overall NHL performance. Hockey performance was determined using a basket of advanced hockey specific metrics that are intended to evaluate a player's overall contribution. In this example, Wins Above Replacement (WAR), Game Score, CorsiFor % and Point Shares were used (advanced hockey analytics were obtained from Corsica.hockey and Hockey-Reference.com). Each advanced stat was calculated as a NHL career average and an average of a player's top three NHL seasons. Player metrics were assigned a percentile rank compared with all other active NHL players in their position over the same time period. For each brain region or network, a machine learning support vector approach was applied to perform the regression modeling, described above. The brain data was regressed against each hockey metric (a total of 8) and the top 5-6 were averaged and combined to derive each primary component score. An example of the performance for each of the See, Process and Move models as well as an overall score is shown in FIG. 11B.

Once the predictive models were generated, the same data processing and extraction techniques were applied to a dataset of 25 prospective NHL players from a WHL team. The algorithms for each of the See, Process, and Move components were applied to the player's MRI data and scores were generated including an overall prediction of athletic potential. A summary of these results is presented in FIG. 11C. The individual scores were plotted against each player's WHL performance (avg. Game Score for the 2016-2017 season). While these metrics were not included in determining the underlying neurological scores, the currents stats can be a rough early guide for the quality of the predictions, although there is not a strong correlation between CHL performance and eventual NHL performance. Of note, two of the top three ranked players were selected in the first round of the 2017 NHL draft. High overall scores to other players selected in the later rounds of the draft (round 3-7). It should be noted that not all of the players were draft eligible yet, including three of the four players given higher performance scores.

The player with the second highest overall score has also not been drafted (indicated by the arrow). This individual scored very highly in the Process and Move components but less well in the See component. More detailed analysis of his scan indicated some inefficiency in his visual system. Based on this data, custom tasks and training programs that an athlete or training staff can use to address any neurologic imbalance or inefficiency identified in the MRI scan were developed to improve performance.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware or with one or more processors programmed using microcode or software to perform the functions recited above.

In this respect, it should be appreciated that one implementation of the embodiments of the present invention comprises at least one non-transitory computer-readable storage medium (e.g., a computer memory, a portable memory, a compact disk, etc.) encoded with a computer program (i.e., a plurality of instructions), which, when executed on a processor, performs the above-discussed functions of the embodiments of the present invention. The computer-readable storage medium can be transportable such that the program stored thereon can be loaded onto any computer resource to implement the aspects of the present invention discussed herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the present invention.

Various aspects of the present invention may be used alone, in combination, or in a variety of arrangements not specifically discussed in the embodiments described in the foregoing and are therefore not limited in their application to the details and arrangement of components set forth in the foregoing description or illustrated in the drawings. For example, aspects described in one embodiment may be combined in any manner with aspects described in other embodiments.

Also, embodiments of the invention may be implemented as one or more methods, of which an example has been provided. The acts performed as part of the method(s) may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing," "involving," and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. A computerized system for predicting performance, the system comprising:
   at least one computer processor; and
   at least one computer-readable medium encoded with a plurality of instructions that, when executed by the at least one computer processor, perform a method of predicting performance of an individual, the method comprising:
   receiving brain imaging data for the individual, wherein the brain imaging data comprises structural brain data;
   determining first values for at least one characteristic of the structural brain data within regions of interest defined for a population of individuals having different performance levels; and
   predicting based, at least in part, on the first values, a performance potential of the individual.

2. The computerized system of claim 1, wherein the structural brain data includes first structural data characterizing white matter structure and second structural data characterizing gray matter structure.

3. The computerized system of claim 2, wherein the first structural data characterizing white matter structure comprises diffusion tensor imaging data.

4. The computerized system of claim 1, wherein the brain imaging data comprises physiological brain data characterizing dynamics of the brain of the individual, and wherein the method further comprises:
   determining second values for at least one characteristic of the physiological brain data within the regions of interest; and
   predicting, based on the second values, a current performance level of the individual.

5. The computerized system of claim 4, wherein the method further comprises:
   determining based, at least in part, on the predicted performance potential and the predicted current performance level, a performance deficit; and
   outputting a training recommendation determined based, at least in part, on one or more characteristics of the performance deficit.

6. The computerized system of claim 4, wherein the physiological brain data includes at least two types of physiological brain data selected from the group consisting of resting state functional connectivity data, cerebral blood flow data, and cerebral vascular reactivity data.

7. The computerized system of claim 1, wherein the brain data includes at least two types of brain data, and wherein the method further comprises:
   creating, a multi-channel voxel map, wherein the multi-channel voxel map associates voxels in each of the regions of interest with multiple values, wherein a first value of the multiple values corresponds to a value determined for a first type of brain data of the at least two types of brain data and a second value of the multiple values corresponds to a value determined for a second type of brain data of the at least two types of brain data.

8. The computerized system of claim 7, wherein the at least two types of brain data includes a first type of structural brain data and a first type of physiological brain data.

9. The computerized system of claim 7, wherein the at least two types of brain data includes a first type of structural brain data and a second type of structural brain data.

10. The computerized system of claim 1, wherein the brain imaging data is data acquired using magnetic resonance imaging.

11. The computerized system of claim 10, wherein the brain imaging data comprises diffusion tensor imaging data.

12. The computerized system of claim 10, further comprising:
    a magnetic resonance imaging system in communication with the at least one computer processor, wherein the magnetic resonance imaging system is configured to acquire the brain imaging data.

13. A computer-implemented method for predicting performance, the method comprising:
    receiving brain imaging data for an individual, wherein the brain imaging data comprises structural brain data;
    determining first values for at least one characteristic of the structural brain data within regions of interest defined for a population of individuals having different performance levels; and predicting, based on the first values, a performance potential of the individual.

14. The computer-implemented method of claim 13, wherein the structural brain data includes first structural data characterizing white matter structure and second structural data characterizing gray matter structure.

15. The computer-implemented method of claim 14, wherein the first structural data characterizing white matter structure comprises diffusion tensor imaging data.

16. The computer-implemented method of claim 13, wherein the brain imaging data comprises physiological brain data characterizing dynamics of the brain of the individual, and wherein the method further comprises:
- determining second values for at least one characteristic of the physiological brain data within the regions of interest; and
- predicting based on the second values, a current performance level of the individual.

17. The computer-implemented method of claim 16, wherein the method further comprises:
- determining based, at least in part, on the predicted performance potential and the predicted current performance level, a performance deficit; and
- outputting a training recommendation determined based, at least in part, on one or more characteristics of the performance deficit.

18. The computer-implemented method of claim 16, wherein the physiological brain data includes at least two types of physiological brain data selected from the group consisting of resting state functional connectivity data, cerebral blood flow data, and cerebral vascular reactivity data.

19. The computer-implemented method of claim 1, wherein the brain data includes at least two types of brain data, and wherein the method further comprises:
- creating, a multi-channel voxel map, wherein the multi-channel voxel map associates voxels in each of the regions of interest with multiple values, wherein a first value of the multiple values corresponds to a value determined for a first type of brain data of the at least two types of brain data and a second value of the multiple values corresponds to a value determined for a second type of brain data of the at least two types of brain data.

20. The computer-implemented method of claim 19, wherein the at least two types of brain data includes a first type of structural brain data and a first type of physiological brain data.

* * * * *